US00PP14202P29

(12) United States Plant Patent
Gitzels

(10) Patent No.: US PP14,202 P2
(45) Date of Patent: Oct. 7, 2003

(54) DAHLIA PLANT NAMED 'MARGARET IMPROVED'

(50) Latin Name: *Dahlia variabilis*
Varietal Denomination: Margare Improved

(75) Inventor: Jeroen Gitzels, Rijsenhout (NL)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/162,995

(22) Filed: Jun. 5, 2002

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—June Hwu
(74) *Attorney, Agent, or Firm*—C. A. Whealy

(57) ABSTRACT

A distinct cultivar of Dahlia plant named 'Margaret Improved', characterized by its upright plant habit; freely branching habit; full and dense plants; double type inflorescences; and yellow-colored ray florets.

1 Drawing Sheet

Botanical classification/cultivar designation: *Dahlia variabilis* cultivar Margaret Improved.

BACKGROUND OF THE INVENTION

The present Invention relates to a new and distinct cultivar of Dahlia plant, botanically known as *Dahlia variabilis,* commercially referred to as a pot-type Dahlia, and hereinafter referred to by the cultivar name 'Margaret Improved'.

The new Dahlia is a product of a planned breeding program conducted by the Inventor in Enkhuizen, The Netherlands. The objective of the breeding program is to create new pot-type Dahlia cultivars with desirable inflorescence form and attractive ray floret coloration.

The new Dahlia originated from a cross-pollination made by the Inventor of two unidentified proprietary *Dahlia variabilis* selections, not patented. The new Dahlia was discovered and selected by the Inventor in September, 1998, as a single flowering plant within the progeny of the stated cross-pollination grown in a controlled environment in Enkhuizen, The Netherlands.

Asexual reproduction of the new Dahlia by vegetative tip cuttings was first conducted in Enkhuizen, The Netherlands in September, 1998. Asexual reproduction by cuttings has shown that the unique features of this new Dahlia are stable and reproduced true to type in successive generations.

SUMMARY OF THE INVENTION

The cultivar Margaret Improved has not been observed under all possible environmental conditions. The phenotype may vary somewhat with variations in environment such as temperature and daylength, without, however, any variance in genotype.

The following traits have been repeatedly observed and are determined to be the unique characteristics of 'Margaret Improved'. These characteristics in combination distinguish 'Margaret Improved' as a new and distinct pot-type Dahlia:

1. Upright plant habit.
2. Freely branching habit, full and dense plants.
3. Double type inflorescences.
4. Yellow-colored ray florets.

Plants of the new Dahlia differ from plants of the parent selections primarily in ray floret coloration.

Plants of the new Dahlia can be compared to plants of the Dahlia cultivar Margaret, disclosed in U.S. Plant Pat. No. 6,769. In side-by-side comparisons conducted in Venhuizen, The Netherlands, plants of the new Dahlia had smaller inflorescences and twice as many ray florets per inflorescence as plants of the cultivar Margaret.

BRIEF DESCRIPTION OF THE PHOTOGRAPH

The accompanying colored photograph illustrates the overall appearance of the new Dahlia showing the colors as true as it is reasonably possible to obtain in colored reproductions of this type. Colors in the photograph may differ from the color values cited in the detailed botanical description which accurately describe the colors of the new Dahlia. The photograph comprises a side perspective view of a typical flowering plant of 'Margaret Improved'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown and flowered during the spring in West Chicago, Ill., under commercial practice in a greenhouse. One cutting was planted per 10-cm container and plants were grown for about 8 weeks.

Botanical classification: *Dahlia variabilis* cultivar Margaret Improved.

Parentage:

*Female, or seed, parent.*—Unidentified proprietary *Dahlia variabilis* selection, not patented.

*Male, or pollen, parent.*—Unidentified proprietary *Dahlia variabilis* selection, not patented.

Propagation:

*Type.*—Terminal tip cuttings.

*Time to rooting.*—About 7 days at 18° C.

*Time to develop a rooted cutting.*—About 28 days at 18° C.

*Root description.*—Fibrous; development of tubers has not been observed.

Plant description:

*Appearance.*—Herbaceous pot-type Dahlia. Inverted triangle; stems mostly upright and somewhat outwardly spreading giving a uniformly mounded appearance to the plant. Freely branching, about five lateral branches per plant; dense and full plants.

*Plant height, soil level to top of inflorescences.*—About 22 cm.

*Plant height, soil level to top of foliar plane.*—About 16 cm.

*Plant width or area of spread.*—About 18.2 cm.

*Lateral branches.*—Length: About 12.5 cm. Diameter: About 4 mm. Internode length: About 2 cm. Strength: Strong. Texture: Smooth, glabrous. Color: 146B.

*Foliage description.*—Arrangement: Opposite; simple. Length: About 6.2 cm. Width: About 4.5 cm. Shape: Ovate. Apex: Acute. Base: Attenuate. Margin: Serrate. Texture, upper and lower surfaces: Smooth, glabrous; leathery. Venation pattern: Pinnate. Petiole length: About 2.5 cm. Petiole diameter: About 3 mm. Petiole texture, upper and lower surfaces: Smooth, glabrous. Color: Young and fully expanded foliage, upper surface: 137A. Young and fully expanded foliage, lower surface: 191A. Venation, upper and lower surfaces: 144C. Petiole, upper and lower surfaces: 144C.

Inflorescence description:

*Appearance.*—Terminal and axillary double type inflorescences held above and beyond the foliage on strong flexible peduncles; inflorescences face mostly upright. Composite inflorescence form with ovate-shaped ray florets and disc florets massed at the center; disc florets inconspicuous; ray and disc florets arranged acropetally on a capitulum. Inflorescences not fragrant. Inflorescences persistent.

*Flowering response.*—Plants flower continuous and freely from spring until fall.

*Postproduction longevity.*—Inflorescences maintain good color and substance for about four to five days on the plant.

*Quantity of inflorescences.*—One inflorescence per peduncle.

*Inflorescence bud* (*stage of showing color*).—Shape: Oblate. Length: About 1.4 cm. Diameter: About 1.5 cm. Color: 1A.

*Inflorescence size.*—Diameter: About 7 cm. Depth (height): About 4 cm. Disc diameter: About 1.4 cm, inconspicious.

*Ray florets.*—Shape: Ovate. Aspect: Straight, concave. Length: About 3 cm. Width: About 2.4 cm. Apex: Acute. Base: Attenuate. Margin: Entire. Texture: Smooth, glabrous. Number of ray florets per inflorescence: About 65. Color: When opening and fully opened, upper surface: 2A. When opening and fully opened, lower surface: 2B.

*Disc florets.*—Shape: Tubular, elongated. Apex: Five-pointed. Length: About 1 cm. Width: About 1 mm. Number of disc florets per inflorescence: About 23. Color: 164A.

*Involucral bracts.*—Quantity: About five. Length: About 1.6 cm. Shape: Rhomboidal. Apex: Acute. Base: Fused. Margin: Entire. Texture: Smooth. Color, upper and lower surfaces: 137A.

*Peduncles.*—Length: About 10.5 cm. Diameter: About 3 mm. Strength: Strong, very flexible. Aspect: Upright. Texture: Smooth, glabrous. Color: 146C.

*Reproductive organs.*—Androecium: Present on disc florets only. Quantity per floret: About four. Anther length: About 4 mm. Anther color: 172C. Filament length: About 6 mm. Filament color: 166A. Pollen color: 168A. Gynoecium: Present on both ray and disc florets. Quantity per floret: One. Pistil length: About 1.3 cm. Stigma length: About 4 mm. Stigma color: 8A. Style color: 154D. Ovary color: 144C.

*Seed/fruit.*—Seed and fruit production has not been observed.

Disease/pest tolerance: Plants of the new Dahlia have not been observed to be tolerant to pathogens and pests common to Dahlias.

It is claimed:

1. A new and distinct cultivar of Dahlia plant named 'Margaret Improved', as illustrated and described.

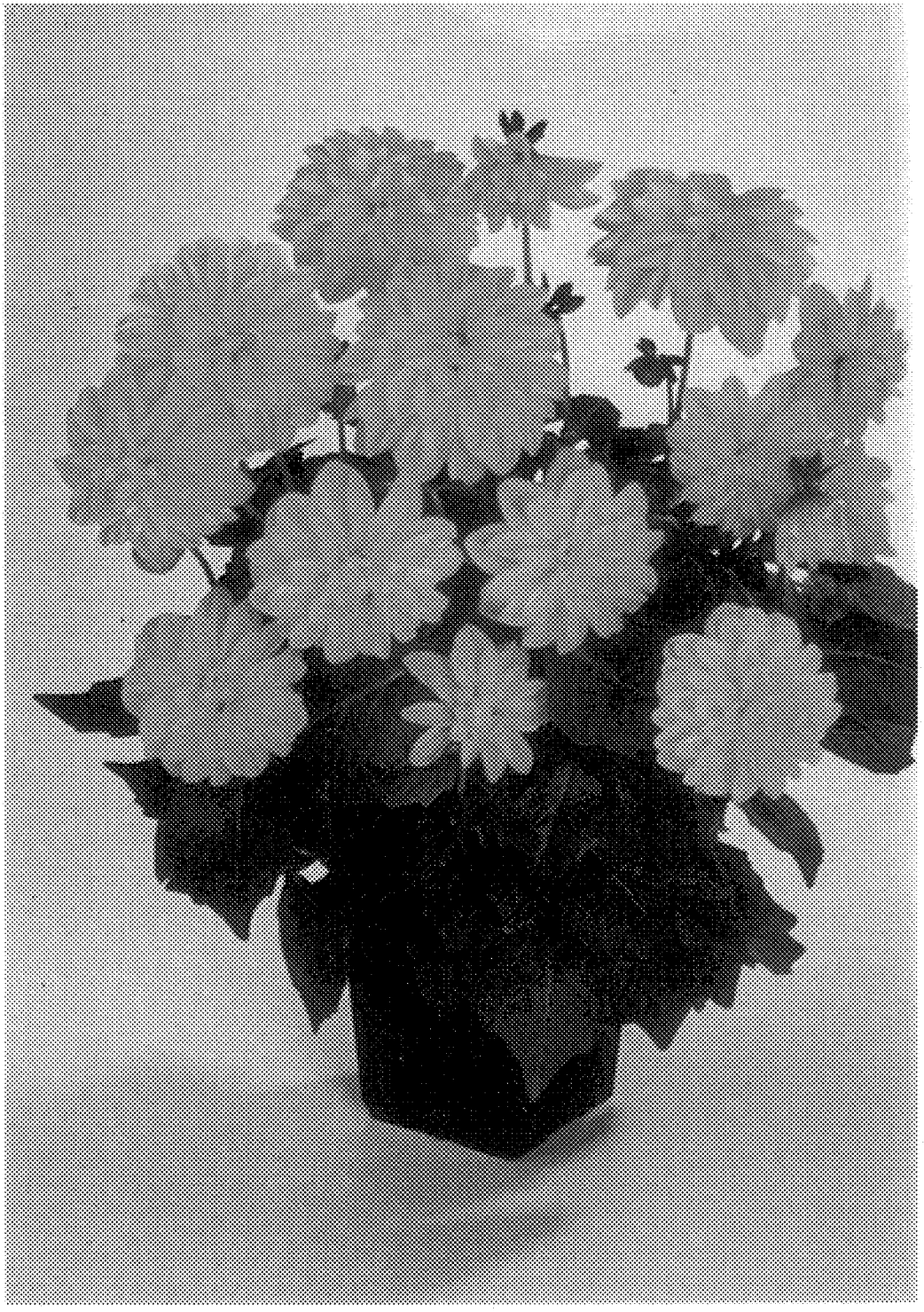

* * * * *